US010561362B2

(12) United States Patent
Reich et al.

(10) Patent No.: US 10,561,362 B2
(45) Date of Patent: Feb. 18, 2020

(54) SLEEP ASSESSMENT USING A HOME SLEEP SYSTEM

(71) Applicant: BOSE CORPORATION, Framingham, MA (US)

(72) Inventors: Debra Reich, Arlington, MA (US); Laura Ware, Boston, MA (US); Jonathan Freed, Milton, MA (US); Jack Read, Bolton, MA (US); Leela Keshavan, Westborough, MA (US); Brian David Mulcahey, Sudbury, MA (US)

(73) Assignee: BOSE CORPORATION, Framingham, MA (US)

(*) Notice: Subject to any disclaimer, the term of this patent is extended or adjusted under 35 U.S.C. 154(b) by 138 days.

(21) Appl. No.: 15/267,886

(22) Filed: Sep. 16, 2016

(65) Prior Publication Data

US 2018/0078198 A1 Mar. 22, 2018

(51) Int. Cl.
*A61B 5/00* (2006.01)
*G16H 40/67* (2018.01)
(Continued)

(52) U.S. Cl.
CPC .......... *A61B 5/4815* (2013.01); *A61B 5/0022* (2013.01); *A61B 5/0205* (2013.01); *A61B 5/4803* (2013.01); *A61B 5/4812* (2013.01); *A61B 5/4818* (2013.01); *A61B 5/4836* (2013.01); *A61B 5/6898* (2013.01); *A61B 5/746* (2013.01); *A61B 7/003* (2013.01);
(Continued)

(58) Field of Classification Search
CPC ... A61B 5/4815; A61B 5/4836; A61B 5/4818; A61B 7/003; A61B 5/4812; A61B 5/0205; A61B 5/6898; A61B 5/746; A61B 5/0022; A61B 5/4803; G16H 40/67; G06F 19/00; A61M 21/02; A61M 2205/3303
See application file for complete search history.

(56) References Cited

U.S. PATENT DOCUMENTS

| 4,228,806 A | 10/1980 | Lidow |
| 5,671,733 A * | 9/1997 | Raviv ............... A61B 7/003 600/301 |

(Continued)

FOREIGN PATENT DOCUMENTS

| CN | 103519784 B | 11/2015 |
| CN | 105231997 A | 1/2016 |

(Continued)

OTHER PUBLICATIONS

International Search Report and Written Opinion for application No. PCT/US2017/051599 dated Jul. 6, 2018.
(Continued)

*Primary Examiner* — Rex R Holmes
(74) *Attorney, Agent, or Firm* — Lando & Anastasi, LLP (57) ABSTRACT

A sleep assessment device is provided for, including biometric sensors for detecting a heart rate, respiration, or movement of a user. The device detect a user's sleep state by reading signals from the biometric sensor and logs detected information in a sleep record. The device then compares the logged information to a thumbprint of sleep patterns indicative of sleep disorders and outputs an indication of potential sleep disorders based on the comparison.

15 Claims, 7 Drawing Sheets

(51) Int. Cl.
  *A61B 5/0205*   (2006.01)
  *A61B 7/00*     (2006.01)
  *A61M 21/02*    (2006.01)
  *A61B 5/0255*   (2006.01)
  *A61B 5/08*     (2006.01)
  *A61B 5/11*     (2006.01)
  *A61B 5/145*    (2006.01)
  *A61M 21/00*    (2006.01)

(52) U.S. Cl.
  CPC ............ *A61M 21/02* (2013.01); *G16H 40/67* (2018.01); *A61B 5/0255* (2013.01); *A61B 5/0803* (2013.01); *A61B 5/1123* (2013.01); *A61B 5/14542* (2013.01); *A61B 5/4806* (2013.01); *A61B 2560/0462* (2013.01); *A61B 2560/0475* (2013.01); *A61B 2562/0204* (2013.01); *A61M 2021/0027* (2013.01); *A61M 2205/3303* (2013.01); *A61M 2205/3306* (2013.01); *A61M 2205/3368* (2013.01); *A61M 2205/3553* (2013.01); *A61M 2205/52* (2013.01); *A61M 2230/06* (2013.01); *A61M 2230/42* (2013.01); *A61M 2230/63* (2013.01)

(56) References Cited

U.S. PATENT DOCUMENTS

| | | | |
|---|---|---|---|
| 5,781,640 A | 7/1998 | Nicolino, Jr. | |
| 5,928,133 A | 7/1999 | Halyak | |
| 6,236,622 B1 | 5/2001 | Blackman | |
| 6,662,032 B1 | 12/2003 | Gavish et al. | |
| 6,825,769 B2 | 11/2004 | Colmenarez et al. | |
| 6,888,779 B2 | 5/2005 | Mollicone et al. | |
| 7,248,915 B2 | 7/2007 | Ronnholm | |
| 7,637,859 B2 | 12/2009 | Lindback et al. | |
| 7,850,619 B2 | 12/2010 | Gavish et al. | |
| 8,243,937 B2 | 8/2012 | Nicolino, Jr. et al. | |
| 8,280,067 B2 | 10/2012 | Nicolino, Jr. et al. | |
| 8,280,068 B2 | 10/2012 | Nicolino, Jr. et al. | |
| 8,285,344 B2 | 10/2012 | Kahn et al. | |
| 8,379,870 B2 | 2/2013 | Nicolino, Jr. et al. | |
| 8,485,982 B2 | 7/2013 | Gavish et al. | |
| 8,550,978 B2 | 10/2013 | Ullmann | |
| 8,562,526 B2 * | 10/2013 | Heneghan | A61B 5/0507 600/301 |
| 8,585,607 B2 | 11/2013 | Klap et al. | |
| 8,731,646 B2 | 5/2014 | Halperin et al. | |
| 8,855,334 B1 | 10/2014 | Lavine et al. | |
| 8,870,764 B2 | 10/2014 | Rubin | |
| 8,870,785 B2 | 10/2014 | Muehlsteff et al. | |
| 8,964,997 B2 | 2/2015 | Gauger, Jr. | |
| 8,992,434 B2 | 3/2015 | Halperin et al. | |
| 9,072,437 B2 | 7/2015 | Paalasmaa | |
| 9,192,326 B2 | 11/2015 | Kahn et al. | |
| 9,192,333 B1 | 11/2015 | Hayes et al. | |
| 2002/0080035 A1 | 6/2002 | Youdenko | |
| 2002/0186618 A1 | 12/2002 | Kirkpatrick | |
| 2003/0095476 A1 | 5/2003 | Mollicone et al. | |
| 2003/0142591 A1 | 7/2003 | Baweja et al. | |
| 2005/0152223 A1 | 7/2005 | Kawakami | |
| 2006/0017558 A1 | 1/2006 | Albert et al. | |
| 2006/0102171 A1 | 5/2006 | Gavish | |
| 2007/0055115 A1 | 3/2007 | Kwok et al. | |
| 2007/0083079 A1 | 4/2007 | Lee et al. | |
| 2007/0249952 A1 | 10/2007 | Rubin et al. | |
| 2008/0157956 A1 | 7/2008 | Radivojevic et al. | |
| 2009/0231964 A1 | 9/2009 | Kraft et al. | |
| 2009/0287109 A1 | 11/2009 | Ferren et al. | |
| 2009/0292222 A1 | 11/2009 | Ferren et al. | |
| 2010/0039399 A1 | 2/2010 | Kim | |
| 2010/0087701 A1 | 4/2010 | Berka et al. | |
| 2010/0162169 A1 | 6/2010 | Skarp | |
| 2010/0226212 A1 | 9/2010 | Gobindram | |
| 2010/0281982 A1 | 11/2010 | Liao | |
| 2011/0004047 A1 | 1/2011 | Braspenning et al. | |
| 2011/0144455 A1 | 6/2011 | Young et al. | |
| 2011/0224510 A1 | 9/2011 | Oakhill | |
| 2011/0230790 A1 | 9/2011 | Kozlov | |
| 2011/0257772 A1 | 10/2011 | Kerber et al. | |
| 2011/0264164 A1 | 10/2011 | Christopherson et al. | |
| 2012/0092171 A1 | 4/2012 | Hwang et al. | |
| 2012/0327748 A1 | 12/2012 | Lee | |
| 2013/0163394 A1 | 6/2013 | Loree, IV | |
| 2013/0234823 A1 | 9/2013 | Kahn et al. | |
| 2013/0289419 A1 | 10/2013 | Berezhnyy et al. | |
| 2013/0289431 A1 | 10/2013 | Gavish et al. | |
| 2013/0338446 A1 | 12/2013 | Van Vugt et al. | |
| 2014/0088373 A1 | 3/2014 | Phillips et al. | |
| 2014/0334645 A1 | 11/2014 | Yun et al. | |
| 2014/0371547 A1 | 12/2014 | Gartenberg et al. | |
| 2014/0371635 A1 | 12/2014 | Shinar et al. | |
| 2015/0141852 A1 | 5/2015 | Dusanter et al. | |
| 2015/0164238 A1 * | 6/2015 | Benson | G16H 50/30 340/540 |
| 2015/0173671 A1 | 6/2015 | Paalasmaa et al. | |
| 2015/0230750 A1 | 8/2015 | McDarby et al. | |
| 2015/0258301 A1 | 9/2015 | Trivedi et al. | |
| 2015/0263688 A1 | 9/2015 | Nicolino, Jr. et al. | |
| 2015/0265212 A1 | 9/2015 | Bruekers et al. | |
| 2015/0320354 A1 | 11/2015 | Oakhill | |
| 2015/0320588 A1 | 11/2015 | Connor | |
| 2015/0367097 A1 | 12/2015 | Gavish | |
| 2016/0015315 A1 | 1/2016 | Auphan et al. | |
| 2016/0055842 A1 | 2/2016 | DeFranks et al. | |
| 2016/0055428 A1 | 3/2016 | Shinar et al. | |
| 2016/0151603 A1 | 6/2016 | Shouldice et al. | |
| 2016/0217672 A1 | 7/2016 | Yoon et al. | |
| 2016/0270718 A1 | 9/2016 | Heneghan et al. | |
| 2016/0335886 A1 | 11/2016 | Wei | |
| 2017/0039045 A1 * | 2/2017 | Abrahami | A61B 5/0205 |
| 2017/0087330 A1 | 3/2017 | Kahn et al. | |
| 2018/0078197 A1 | 3/2018 | Ware et al. | |
| 2018/0078198 A1 | 3/2018 | Reich et al. | |
| 2018/0078732 A1 | 3/2018 | Keshavan et al. | |
| 2018/0078733 A1 | 3/2018 | Freed et al. | |
| 2018/0081527 A1 | 3/2018 | Dolecki et al. | |
| 2018/0082550 A1 | 3/2018 | Read et al. | |

FOREIGN PATENT DOCUMENTS

| | | | |
|---|---|---|---|
| EP | 2278507 A2 | 1/2011 | |
| EP | 2976993 A2 | 1/2016 | |
| JP | 2007244597 A | 9/2007 | |
| WO | 2005084538 A1 | 9/2005 | |
| WO | 2012051630 A2 | 4/2012 | |
| WO | 2013093712 A1 | 6/2013 | |
| WO | 2013134160 A2 | 9/2013 | |
| WO | 2015006364 A2 | 1/2015 | |
| WO | 2015008285 A1 | 1/2015 | |
| WO | 2015061579 A1 | 4/2015 | |
| WO | 2016035073 A1 | 3/2016 | |
| WO | 2016122143 A1 | 8/2016 | |
| WO | 2016142793 A1 | 9/2016 | |

OTHER PUBLICATIONS

Android Headlines: "Samsung Galaxy S5—How to Set an Alarm", YouTube, Apr. 28, 2014, pp. 1-3, XP054978390, Retrieved from the Internet: URL:https://www.youtube.com/watch?v=d8MT5Y5US18.
International Search Report and Written Opinion for application No. PCT/US2017/051617 dated Dec. 1, 2017.

* cited by examiner

SLEEP ASSESSMENT USING A HOME SLEEP SYSTEM

CROSS-REFERENCE TO RELATED APPLICATIONS

This application relates to U.S. patent application Ser. No. 15/267,464 entitled Sleep Quality Scoring and Improvement; U.S. patent application Ser. No. 15/267,552 entitled Intelligent Wake-Up System; U.S. patent application Ser. No. 15/267,567 entitled Sleep Assistance Device; U.S. patent application Ser. No. 15/267,848 entitled Sleep System; and to U.S. patent application Ser. No. 15/267,858 entitled User Interface for a Sleep System; all of which are filed on even date herewith and are incorporated herein by reference.

FIELD

This disclosure relates to systems, methods, and apparatuses for performing sleep assessments using a sleep monitoring device in order to provide sleep assessment information to a user and/or a healthcare professional.

BACKGROUND

Sleeplessness and poor or interrupted sleep may significantly affect a person's health. Poor sleep may be caused by such factors as sleep apnea, sleep walking, sleep talking, and/or snoring. Thus, there exists a need for a device that can monitor sleep patterns for assessing potential sleeping disorders in a user without requiring that the user visit a sleep lab to undergo a study.

SUMMARY

This disclosure relates to systems, methods, and apparatuses for assessing sleep using a sleep monitoring device in order to provide information to users or medical professionals regarding potential sleep disorders detected by the system.

All examples and features mentioned below can be combined in any technically possible way.

In one example of this disclosure, a sleep assessment device is provided for, including at least one biometric sensor for detecting at least one of a heart rate, respiration, or movement of a user; a processor; memory. The processor is configured to detect a user's sleep state by reading signals from said at least one biometric sensor. The processor is also configured to log information in a sleep record, including biometric information detected during the period a user is sleeping. The processor is also configured to compare the logged information in said sleep record to a thumbprint of sleep patterns and output an indication of potential sleep disorders based on the comparison. In some examples, the sleep assessment device may also include a microphone. The thumbprint may also be a thumbprint of a normal sleep pattern or a thumbprint of a known sleep disorder. The sleep disorder may be sleep apnea, sleep talking, sleep walking, or snoring.

In other examples, the processor may also be configured to output a notification of a potential sleep disorder. The sleep assistance device may also include a transmitter for transmitting the notification of a potential sleep disorder. The sleep assessment device may also include at least one direct biometric sensor and the processor may be configured to detect a user's sleep state by reading signals from the at least one direct biometric sensor. In some implementations, the at least one direct biometric sensor may be a blood oxygen sensor. The processor is may also be configured to detect sound while a user is sleeping and log sound information into said sleep record.

A method for providing an indication of a potential sleep disorder is also provided for including the steps of providing at least one contactless biometric sensor for detecting at least one of a heart rate, respiration, or movement of a user; detecting a user's sleep state by reading signals from said at least one contactless biometric sensor; logging information in a sleep record, including biometric information relating to the quality of a user's sleep; comparing the logged information in the sleep record to a thumbprint of sleep patterns; determining whether a potential sleep disorder exists based on the comparison; and providing an indication that a potential sleep disorder exists. In some examples the method may also include providing at least one direct biometric sensor and reading signals from the at least one direct biometric sensor. In some examples, the at least one direct biometric sensor may be a blood oxygen sensor. In some implementations, the method may also include providing at least one microphone; reading signals from the at least one microphone; and logging sound information in the sleep record.

A sleep latency assessment device may also be provided for, including at least one biometric sensor for detecting at least one of a heart rate, respiration, or movement of a user; a processor; and memory. The processor may be configured to detect a user's sleep state by reading signals from the at least one biometric sensor. The processor may also be configured to provide a sleep signal and record the amount of time after the sleep signal is provided before the biometric sensor indicates that the user has fallen asleep. The processor may also be configured to provide an alarm signal a predetermined amount of time after a user has fallen asleep. In some examples, the processor may also be configured to provide at least a second sleep signal after a user has awoken and record the amount of time after the second sleep signal is provided before the biometric sensor indicates that the user has fallen asleep a second time. The processor may also be configured to determine whether additional sleep latency assessment cycles are required based on predetermined sleep latency assessment criteria. In other examples, the processor may also be configured to generate a sleep latency assessment report based on at least one sleep latency assessment cycle.

A method for assisting a user sleep may also be provided, including the steps of providing a sleep assistance device comprising at least one speaker, at least one microphone, a processor, and at least one biometric sensor for detecting at least one of a heart rate, respiration, or movement of a first user; determining that a first user has fallen asleep based on signals received from the biometric sensor; detecting sounds emanating from the first user through the microphone; determining a noise-masking sound based on the detected sounds emanating from the first user; and playing the noise-masking sound through the at least one speaker for assisting a second user sleep.

BRIEF DESCRIPTION OF THE DRAWINGS

Various aspects of at least one implementation of a sleep assessment system are discussed below with reference to the accompanying figures. The figures are provided for the purposes of illustration and explanation and are not intended as a definition of the limits of the disclosure.

DETAILED DESCRIPTION

It should be understood that the following descriptions are not intended to limit the disclosure to an exemplary implementation. To the contrary, it is intended to cover alternatives, modifications, and equivalents as may be included within the spirit and scope of the described subject matter.

Figure 1A:
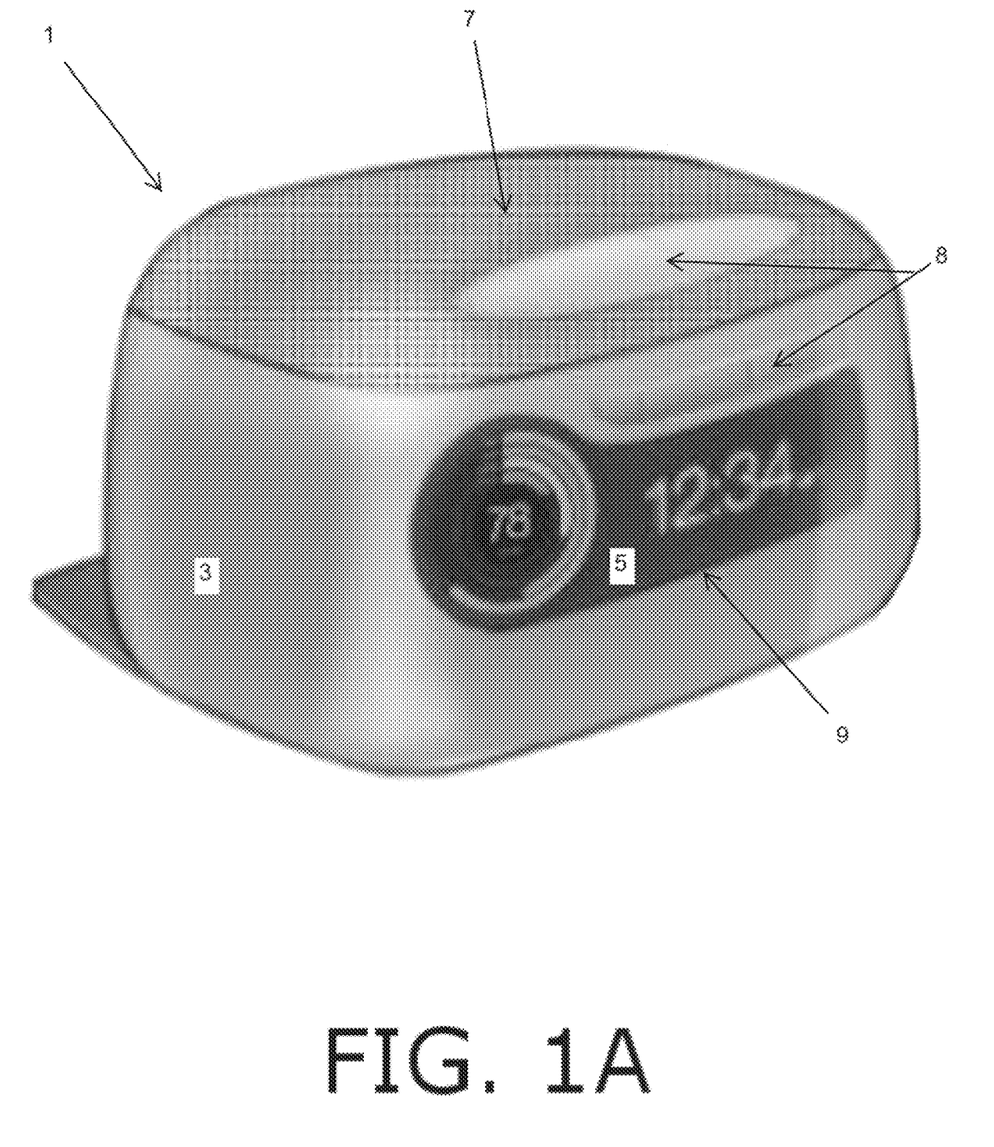
FIG. 1A is a front perspective view of a sleep assessment device with a rectangular housing in one example of the present disclosure.
Figure 1B:
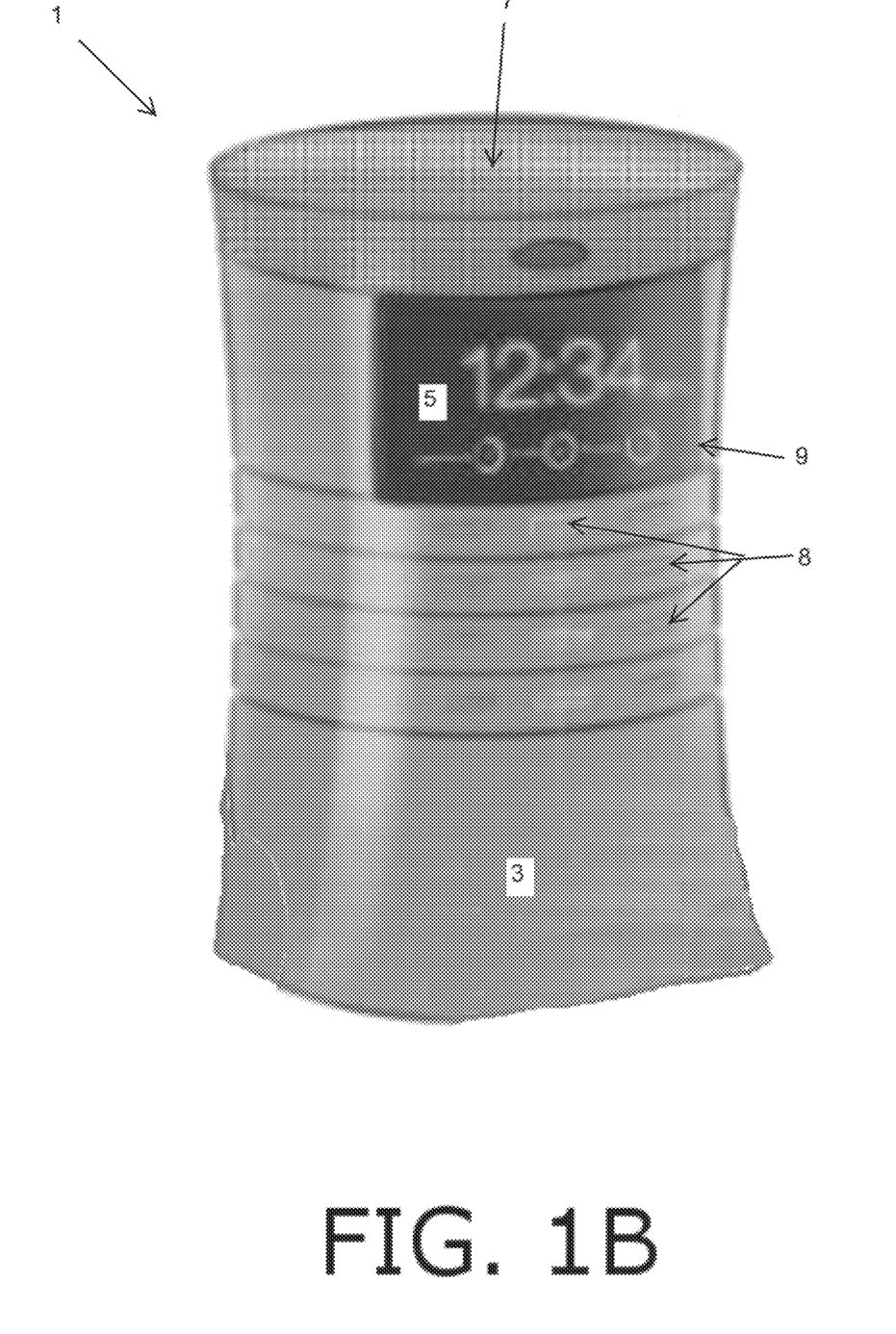
FIG. 1B is a front perspective view of a sleep assessment device with a cylindrical housing in one example of the present disclosure.
Figure 1C:
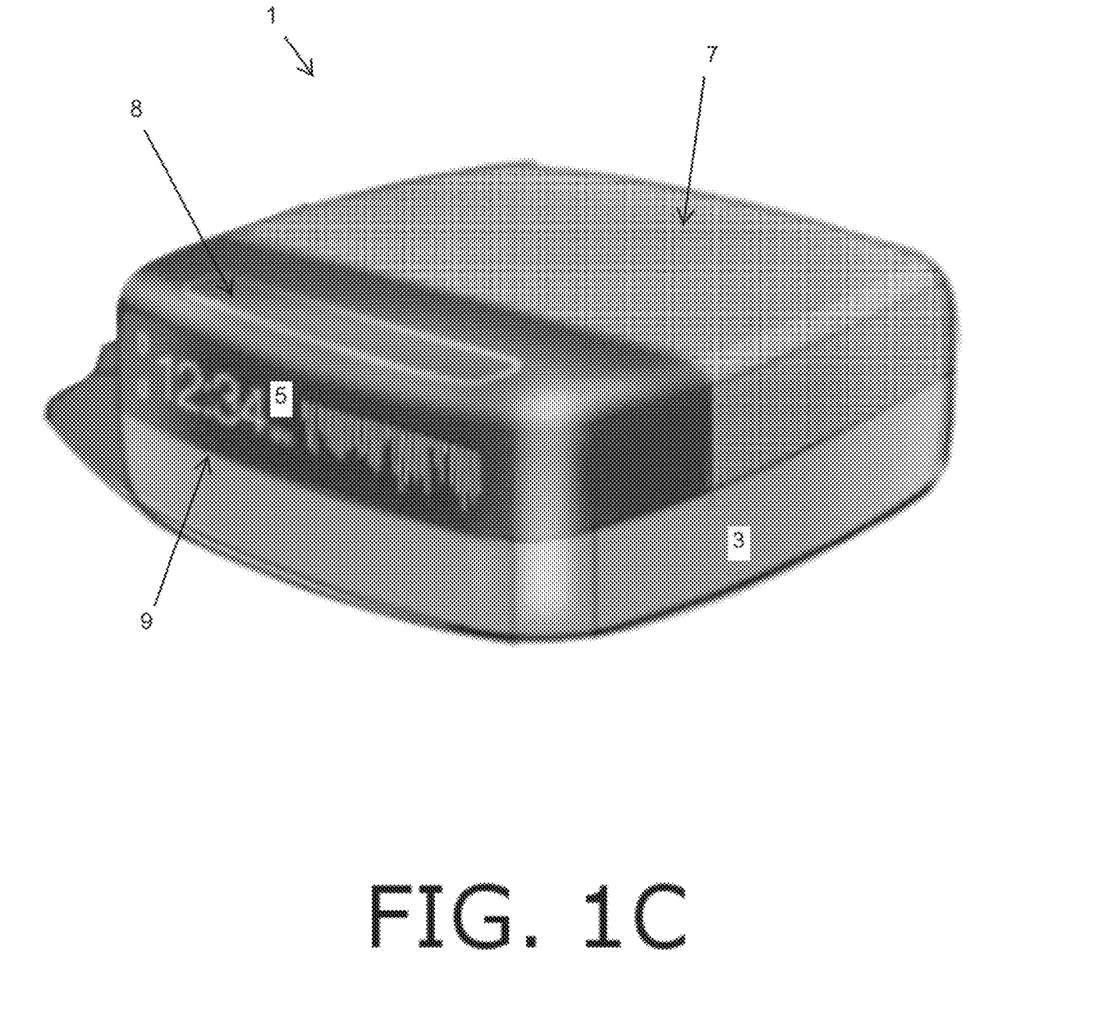
FIG. 1C is a front perspective view of a sleep assessment device with a square housing in one example of the present disclosure.

FIGS. 1A-1C are front perspective views of a sleep assessment device 1 in three examples of the present disclosure. As shown, a sleep assessment device 1 may include a housing 3, a display screen 5, speakers 7, and buttons 8 or a touchscreen 9 for inputting information into the sleep assessment device. A wide variety of forms may be utilized for a sleep assessment device, including a rectangular shape (e.g. FIG. 1A), an elongate cylindrical tower (e.g. FIG. 1B), or a flat square shape (e.g. FIG. 1C). However, as one of ordinary skill in the art will appreciate, any suitable form factor may be utilized that may be suitable for being placed nearby a user while sleeping, such as on a night stand, for example. In such examples, housing 3 may be formed into a suitable shape from any rigid materials, including plastics, metals, wood, or composites.

In some examples, a display screen 5 may b provide biometric or sleep information gathered by sleep assessment device 1 that may be of interest to a user. Such information may include information regarding the user's biometrics observed during sleep periods, such as information regarding the user's presence, heart rate, heart rate variability, respiratory rate, ambient temperature, movement, snoring, or sleep state over time. This may be direct information or derived information. In some examples, user interface screen 5 may also include a clock as shown, for example, in FIGS. 1A-1C.

Speakers 7 may comprise any suitable speaker system for generating sounds, as may be familiar to one of ordinary skill in the art. In some examples, speakers 7 may comprise an upwards firing driver along with an acoustic deflector, to provide an omni-directional acoustical experience. Such configurations may be helpful for providing non-directional, room-filling sounds for a soundscape or a white noise while a user is sleeping. Omni-directional sounds systems may be particularly helpful to achieve soothing sounds, a natural wake-up experience, and a consistent listening experience throughout the room. As one of ordinary skill in the art will appreciate, any acceptable sound system for speakers 7 may be employed for producing room-filling sounds, however.

Touchscreen 9 or buttons 8 may comprise any suitable means for delivering inputs to sleep assessment device 1, including a tactile sensor coupled to a surface of housing 3 for detecting the presence of a user's fingers and for detecting pressure, such as when a virtual button on touchscreen 9 is being pressed by a user. Virtual buttons may be displayed on touchpad 9 in a manner familiar to one of ordinary skill in the art in order to allow an operating system to accept input commands from a user. In this manner, sleep assessment device 1 may be configured to accept input commands in a variety of ways and in a variety of contexts, by providing a programmable user interface that may present options and choices to a user via touchpad 9. In other examples, touchscreen 9 may present a permanent display of fixed virtual buttons or include fixed physical buttons 8 for receiving inputs from a user.

In some examples, display screen 5 and a touchscreen 9 may not be necessary or may be reduced in function because a user's smartphone or other external computing device may be used for linking with sleep assessment device 1, displaying information from sleep assessment device 1 and/or accepting inputs and delivering them to sleep assessment device 1 in order to control its functions. In such a configuration, the display screen 5 and touchscreen 9, if any, may display and control only typical bedside clock-related functions, such as time, alarm, and music selection, or a simplified component of the sleep score, such as just a total score value, may be displayed.

Figure 2:
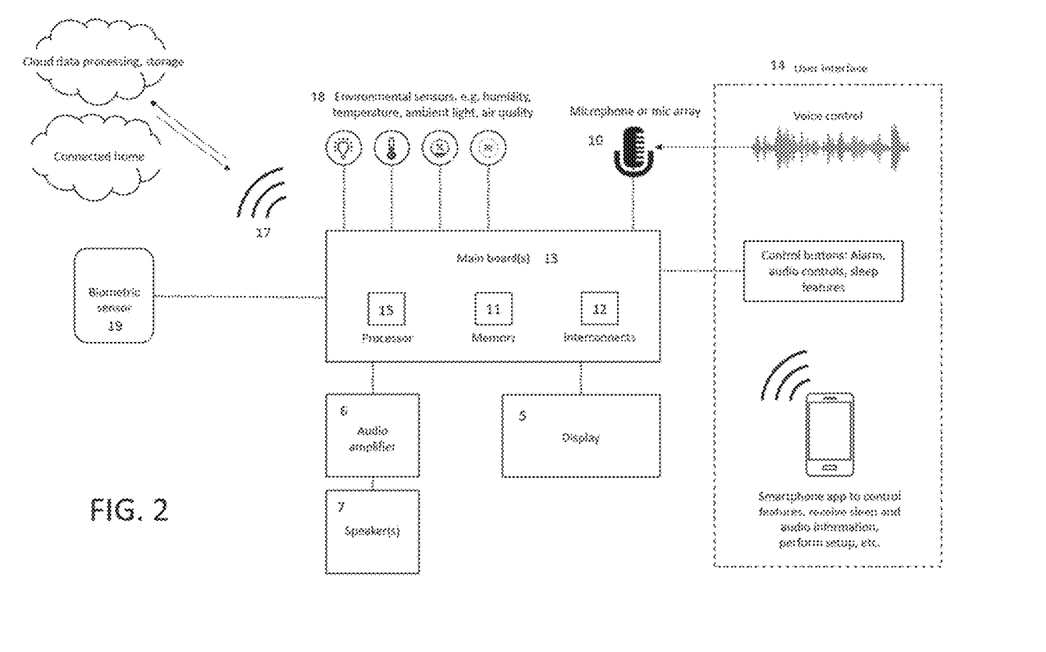
FIG. 2 is a schematic of the components of a sleep assessment device in one example of the present disclosure.

FIG. 2 provides an exemplary schematic of a sleep assessment device, showing its components. As shown, sleep assessment device 1 may include one or more main board(s) 13, including a processor 15, memory 11, and interconnects 12. Main board 13 controls the operation of several other connected components, such as a microphone 10, display screen 5, audio amplifier 6, speakers 7, and buttons 8 or a touchscreen 9 for inputting information into the sleep assistance device. Communications hardware 17 may include any wired or wireless communication means suitable for use with a sleep assessment device, such as WiFi, Bluetooth, USB, micro USB, or any suitable wired or wireless communications technologies known to one of ordinary skill in the art. Main board 13 also receives information from biometric sensor 19 as well as any number of environmental sensors 18, for detecting environmental conditions, such as temperature, humidity, ambient light, and air quality. Main board 13 also receives inputs based on a user's interactions with a user interface 14, which may include voice-activated commands detected by microphone 10; various audio, alarm, and sleep control inputs received from buttons 8 or touchscreen 9; or inputs received from a companion application running on a user's smart phone or other external computing device. The communications hardware 17 may also provide communications with external data sources, such as weather reports, and connected home services providing access to such things as lights, thermostat, locks, and any of the sensors 18.

Microphone 10 may be any suitable microphone for detecting and sampling sounds within a user's bedroom or sleep space, as is known to one of ordinary skill in the art. In some examples, microphone 10 may be an arrayed microphone that is suitable for distinguishing between sounds produced by sleep assessment device 1 and sounds produced externally within the user's bedroom or sleep space. In examples where microphone 10 comprises an arrayed microphone, it may comprise a plurality of omni-directional microphones, directional microphones, or any mixture thereof, distributed about sleep assessment device 1.

Microphone 10 may be coupled to processor 15 for simultaneous processing of the signals from each individual microphone in a manner familiar to one of ordinary skill in the art in order to distinguish between sounds produced by sleep assessment device 1 and other sounds within the room and to analyze any external noises for use with sound-masking subroutine 27, as discussed below. Microphone 10 may employ beamforming or other techniques to achieve directionality in a particular direction, for example, towards a sound to be analyzed. Microphone 10 may be employed both for monitoring the user's sleep and for receiving spoken user interface commands.

Biometric sensor 19 remotely detects information about a nearby user, including bed presence, respiration rate, heart rate, heart rate variability, or a sleep state among other biometric indicators. In some examples, biometric sensor 19 may be a contactless biometric sensor which may use an internal RF sensor for directing RF signals towards a user, measuring the strength of the backscattered signal, and analyzing the backscattered signal to determine the state of various vital signs of a user over time. Other contactless biometric techniques may include lasers for measuring minor skin deflections caused by a user's heart rate and blood pressure; or image-based monitoring systems, whereby skin deflections caused by heartbeats and blood pressure may be observed and analyzed over time through a camera. Biometric sensor 19 may be configured to report detected biometric information to processor 15 for storage in memory 11 and to be analyzed for use in the various subroutines described herein.

In other examples, sleep assessment device 1 may also employ a direct biometric sensor as is known to one of ordinary skill in the art. A direct biometric sensor may include probes or contact pads, that may be disposed on or under the user's body or within their mattress or sheets in order to mechanically detect biometric information, such as movement, respiration, heart rate, blood pressure, and temperature, among others. Such sensors may include accelerometers, other motion sensors, or mechanical sensors such as piezoelectric sensors or other vibration sensors. In other examples, a direct biometric sensor probes may include a blood oxygen sensor (or oximeter). The oximeter may be a sensor that relies on transmissive pulse oximetry and/or reflectance pulse oximetry. The oximeter is useful for detecting a blood oxygen level in a user and for detecting potential hypoxemia in a user. The biometric information detected by the probes may then be communicated to sleep assessment device 1 using a wired or wireless connection in a manner known to one of ordinary skill in the art. In some examples, a biometric sensor may be placed within earbuds worn by a user. Other implementations may combine both contactless and direct biometric sensors. Mechanical sensors that measure the body through an intervening medium, such as bedding, are included in the category of "contactless" biometric sensors.

In some examples, the processor 15 detects a user's sleep state by reading signals from the at least one biometric sensor 19, logs information in a sleep record in memory (or another storage device) 11, including biometric information relating to the quality of a user's sleep. The processor may also output an assessment of potential sleep disorders based on the logged information in the sleep record. Examples of potential sleep disorders that may be observed by various implementations of the sleep assessment device include sleep apnea, sleep talking (somniloquy), sleep walking (somnambulism or noctambulism), and snoring. As discussed in relation to the systems and methods described below, some implementations of the sleep assessment device may output a sleep assessment that is based on a comparison of the logged information in the sleep record to a thumbprint of a normal or abnormal sleep pattern.

At least one thumbprint of normal sleep patterns or at least one the thumbprint of one or more known sleep disorders can be stored in the memory 11. The computer readable memory 11 can store thumbprints that are sound files, databases, or other files capable of storing information relating to any biometric indicators of a potential sleep disorder, including sounds, respiration signatures, pulse signatures, among others. The thumbprint may include time domain or frequency domain data for comparison to time domain r frequency domain data observed by the at least one contactless sensor or a direct sensor of the sleep assessment device.

In some examples, processor 15 may assess potential sleep disorders based on measured characteristics of a sleep record. For example, the processor may detect periods of increased movement of the user, periods of decreased movement of the user, a length of time between movements of the user, a period of time of irregular respiration, a period of time of no respiration, a period of time of irregular pulse, a period of time of no pulse, or other periods of time during which there is an indicator of disrupted sleep, depending on what sensors are in communication with the processor 15. In some examples, processor 15 may detect periods of decreased blood oxygen levels in implementations where an oximeter is employed as a biometric sensor. When these measured characteristics for a user are consistent with a sleep disorder, the processor 15 may identify the potential sleep disorder in the user and indicate that the user should further investigate whether he or she may be diagnosed with the respective sleep disorder in order to seek treatment.

In some examples, the processor 15 may output a notification of a potential sleep disorder to a user. In such examples, the communications hardware 17 may be in communication with the processor and may transmit the output sleep assessment data to another electronic device. The system, device, and method of this disclosure are each useful for approximating a sleep lab in the convenience of a user's home. The system and method may also useful for producing a sleep assessment report for a healthcare professional. This report may be transmitted to a doctor or other healthcare professional at a remote location using the communications hardware 17. Alternatively, a doctor or other healthcare professional may be granted permission to access or download the information stored in a sleep record in memory 11.

In other implementations, the sleep assessment device may provide sleep improvement tips to a user. In such implementations, the system may include a coaching application that sheds light on a user's sleep patterns, identifying both major and minor changes that the user can make to get better rest as disclosed, for example, in U.S. patent application Ser. No. 15/267,464, the disclosures of which are incorporated herein by reference. In such examples, where sleep assessment device 1 determines that user behaviors either ameliorate or exacerbate a potential sleep disorder, the system may also provide coaching tips to help address a detected sleep disorder.

Figure 3:
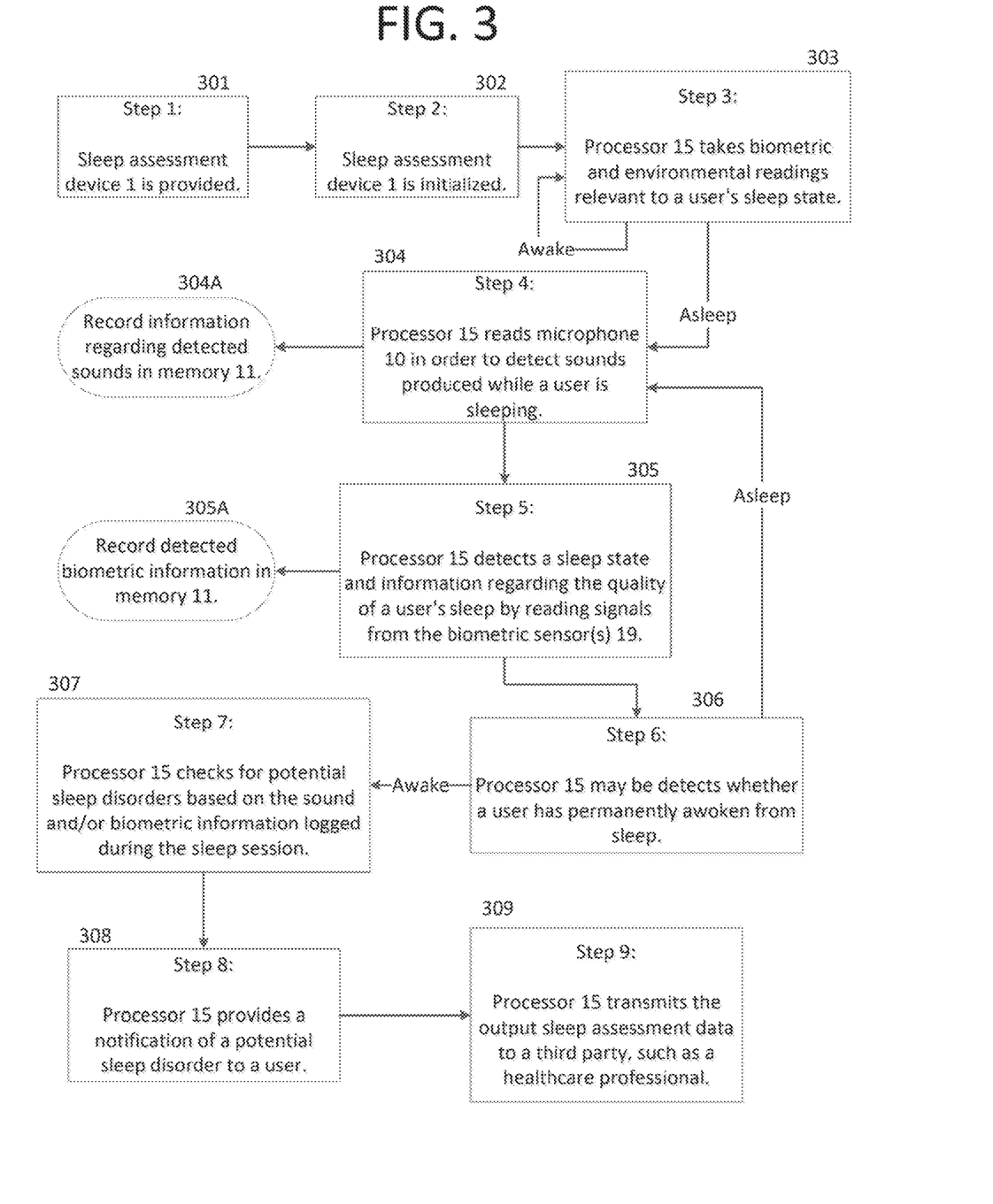
FIG. 3 is a flowchart showing a potential sequence of steps for a sleep assessment program in one example of the present disclosure.

FIG. 3 shows an example of a method for assessing a user's sleep for potential sleep disorders. At step 1 (box 301 in FIG. 3), a sleep assessment device is provided, including at least one biometric sensor for detecting at least a heart rate of a user, respiration of a user, and movement of a user; a microphone 10 for detecting sounds within a bedroom or sleep space; and a processor 15 coupled to memory 11, which may store information regarding potential sleep disorders, such as a sleep disorder thumbprint, as described above. Each biometric sensor may be a contactless biometric sensor or a direct biometric sensor or a mixture of contactless and direct biometric sensors. In step 2, the sleep assessment device, including the at least one biometric sensor is initialized (box 302).

Once initialized, sleep assessment device 1 may begin taking biometric and environmental readings relevant to a user's sleep state. For example, at step 3, processor 15 reads signals from biometric sensor(s) 19 to determine when a user has achieved sleep (box 303). At step 4, once a user has achieved sleep, processor 15 reads microphone 10 in order to detect sounds produced while a user is sleeping (box 304). Any detected sound information may be logged into a sleep record which may be a database of information recorded or detected by sleep assessment device 1 throughout a sleep session (box 304A). In some examples, the acoustic characteristics of a sound (e.g. pitch, volume, duration) may be recorded in the sleep record. In other examples, the sound itself may be recorded and saved within the sleep record for future analysis by a user or a healthcare professional. At step 5, processor 15 detects a user's sleep state and information regarding the quality of a user's sleep by reading signals from the biometric sensor(s) 19 (box 305). Data received by processor 15 from the biometric sensor(s) may be logged in a sleep record (box 305A). In some implementations steps 4 and 5 proceed simultaneously in parallel.

At step 6, processor 15 detects whether a user has permanently awoken from sleep, signaling the end of a sleep session (box 306). To do so, processor 15 may continually monitor the biometric readings provided by biometric sensor(s) 19 in order to determine whether a user has awoken or left their bed. If so, processor 15 may continue monitoring biometric information for a predetermined period of time (e.g. 20 minutes) to determine whether the user has returned to sleep. If so, processor 15 may return to steps 4 and 5 until detecting another waking event. Alternatively, if the user does not return to sleep, processor 15 may determine that the sleep session has ended and discontinue readings from biometric sensor 19.

In step 7, processor 15 may be configured to check for potential sleep disorders once the sleep session has concluded, based on the sounds or biometric information logged in the sleep record during the sleep session (box 307). This can be achieved by comparing the logged information to thumbprints of known sleep disorders stored in memory 11, or measuring characteristics of the logged information in the sleep record, as discussed above. In some examples, an assessment of a potential sleep disorder may be based on a comparison between the logged information in the sleep record to a thumbprint of a normal sleep pattern. The thumbprint may be a sample of time domain data or frequency domain data. Where a thumbprint is used, processor 15 may compare at least a subset of the logged information to the normal thumbprint. If there is a match between the logged information and the normal sleep thumbprint the user's sleep may be confirmed as being within normal parameters. If there is not a match between the logged information and the normal sleep thumbprint, the user's sleep may be assessed as abnormal.

In some examples, an assessment of a potential sleep disorder may be based on a comparison of the logged information in the sleep record to an abnormal thumbprint of a known sleep disorder. As described above, the thumbprint of a known sleep disorder may be time domain data or frequency domain data, although any suitable form of a thumbprint may be utilized as is known to one of ordinary skill in the art. Such time domain data or frequency domain data may reflect biometric information over time known to be an indication of a potential sleep disorder, such as heartrate, respiration rate, detected sound characteristics, movement, or blood oxygen levels, among others, known to be consistent with a sleep disorder. Where an abnormal thumbprint is used, processor 15 may be configured to compare at least a subset of the logged information to the thumbprint of a known sleep disorder. If there is a match between the logged data and the abnormal thumbprint, the user's sleep may be assessed as abnormal or as consistent with a disorder. If there is no match between the two, the user is may be assessed to be an unlikely candidate for the respective sleep disorder.

In some examples, the sleep disorder may be a sleep apnea, sleep talking, sleep walking, or snoring. Other potential sleep disorders may also be assessed, and respective thumbprints may be provided for those additional disorders. In some examples, the method can employ more than one thumbprint, so that the method is capable of assessing a user with a first sleeping disorder based on matching logged data to a first thumbprint, the method is capable of assessing a user for a second sleeping disorder based on matching logged data to a second thumbprint, and the method is capable of assessing a user with a third sleeping disorder based on matching logged data to a third thumbprint, and so on.

The method may further comprise a step 8 for providing a notification of a potential sleep disorder to a user. In some examples, this can be done by displaying the notification on the touchscreen 9 of the device 1. In other examples, this can be done by transmitting the notification to another device, such as a cell phone, a tablet, or another electronic device or to an email address of a user. Step 8 may also include providing notifications that include sleep coaching tips generated by the processor 15 of the device. For example, in step 8, processor 15 may be configured to provide suggestions for changes the user can make to improve his or her sleep or potentially ameliorate the symptoms of a detected potential sleep disorder, and generate suggestions of features of the system that the user can leverage to improve their sleep (box 308).

In some examples, the method may also include step 9 for transmitting the output sleep assessment data through communications hardware 17 to a third party, such as a healthcare professional (box 309). This sleep assessment data may be received by another device, where it can be stored in memory or another storage device, and can be displayed to a user. In other examples, a user's sleep record may be maintained on sleep assessment device 1, but permission for third parties (e.g. a doctor or healthcare professional) to access the information via a network may be granted by a user. Such information may be useful for a healthcare professional to diagnose a potential sleep disorder or continue to monitor a user's progress during treatment for an already-diagnosed sleep disorder.

Some examples of step 2 of method 200 may include activating sensors for sensing a blood oxygen level of a user (box 302). In such examples, step 5 may include detecting a user's blood oxygen level (box 305). As one of ordinary skill in the art will appreciate, sleep apnea may be indicated by a cessation of breathing along with a 4% drop in blood oxygen level. The processor 15 is capable of identifying such symptoms collected by the biometric sensor(s) that correspond to sleep apnea, and is capable of determining that the user has sleep apnea or potentially has sleep apnea.

In other examples, step 5 may include detecting the number of times that the user awakens during the night (box 305). The number of awakening events can be displayed on the touchscreen 9 of the device 1 and recorded in a user's sleep record for later analysis.

Figure 4:
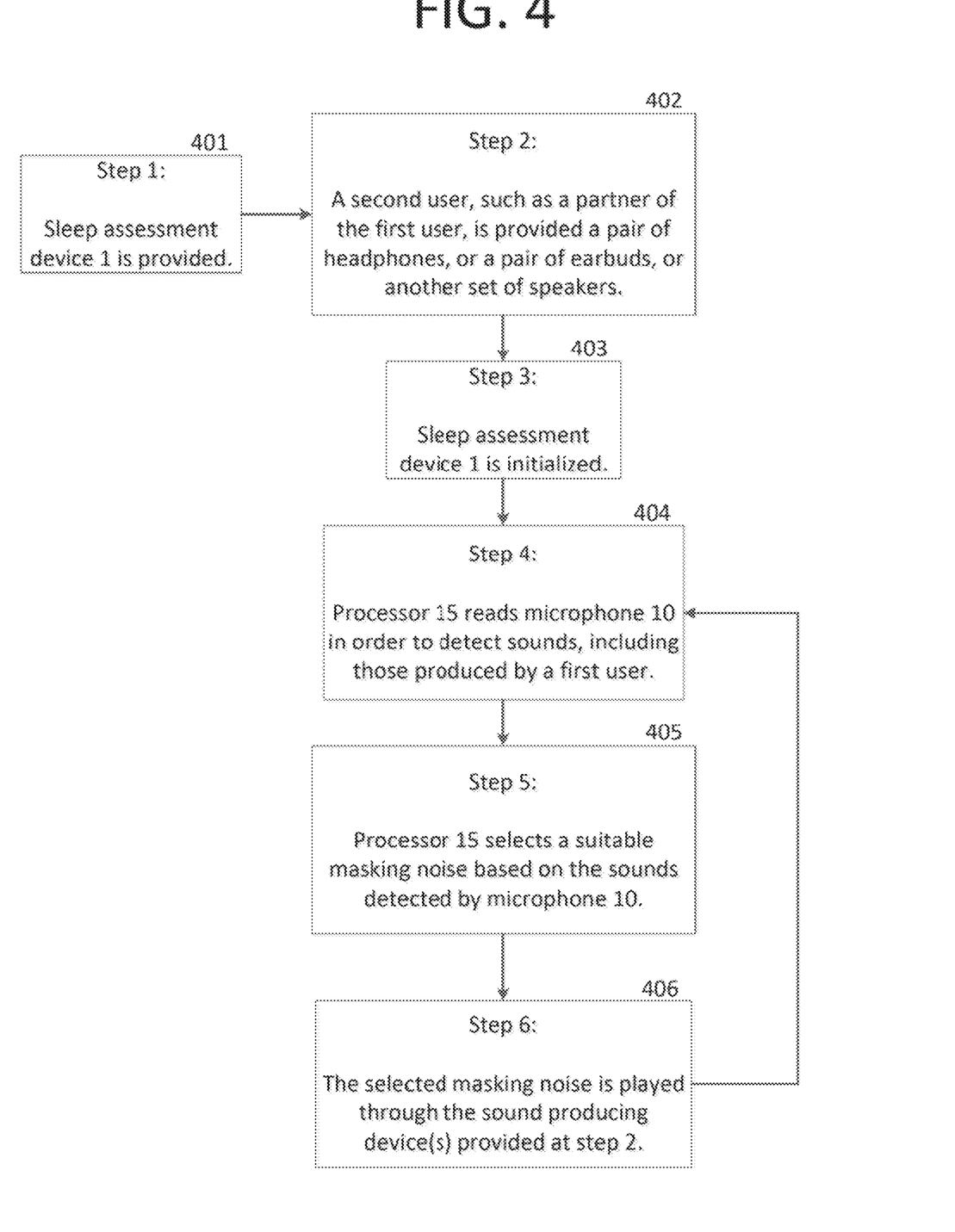
FIG. 4 is a flowchart showing a potential sequence of steps for a partner noise masking program in one example of the present disclosure.

FIG. 4 shows an example of a method for improving the sleep quality of the partner of a user who snores or makes noise during the night, for example, through movement. At step 1, a sleep assessment device is provided, including at least one microphone 10 for detecting sounds within a bedroom or sleep space; and a processor 15 coupled to memory 11, which may be configured to generate noise-masking sounds based on detected noises in a manner known to one of ordinary skill in the art (box 401 in FIG. 4). At step 2, a second user, who may be the partner of the first user, is provided with a pair of headphones, or a pair of earbuds, or another set of speakers for directing a masking sound to the partner's ears (box 402). In step 3, the sleep assessment device, including the at least one microphone is initialized (box 403).

At step 4 microphone 10 may detect sounds occurring within the bedroom or sleep space during the night, including noises created by a first user of the device (box 404). At step 5, processor 15 selects a suitable masking noise based on the sounds detected within the room or sleep space, including sounds emanating from the first user (box 405). A masking sound may be a sound such as white noise. At step 6, noise-masking sounds may be played through the sound producing device(s) provided at step 2 (box 406). In some examples, the sound producing device(s) used by the partner may additionally provide noise-cancelling signals, which may be modified according to the noise-masking sounds provided by the sleep system.

Figure 5:
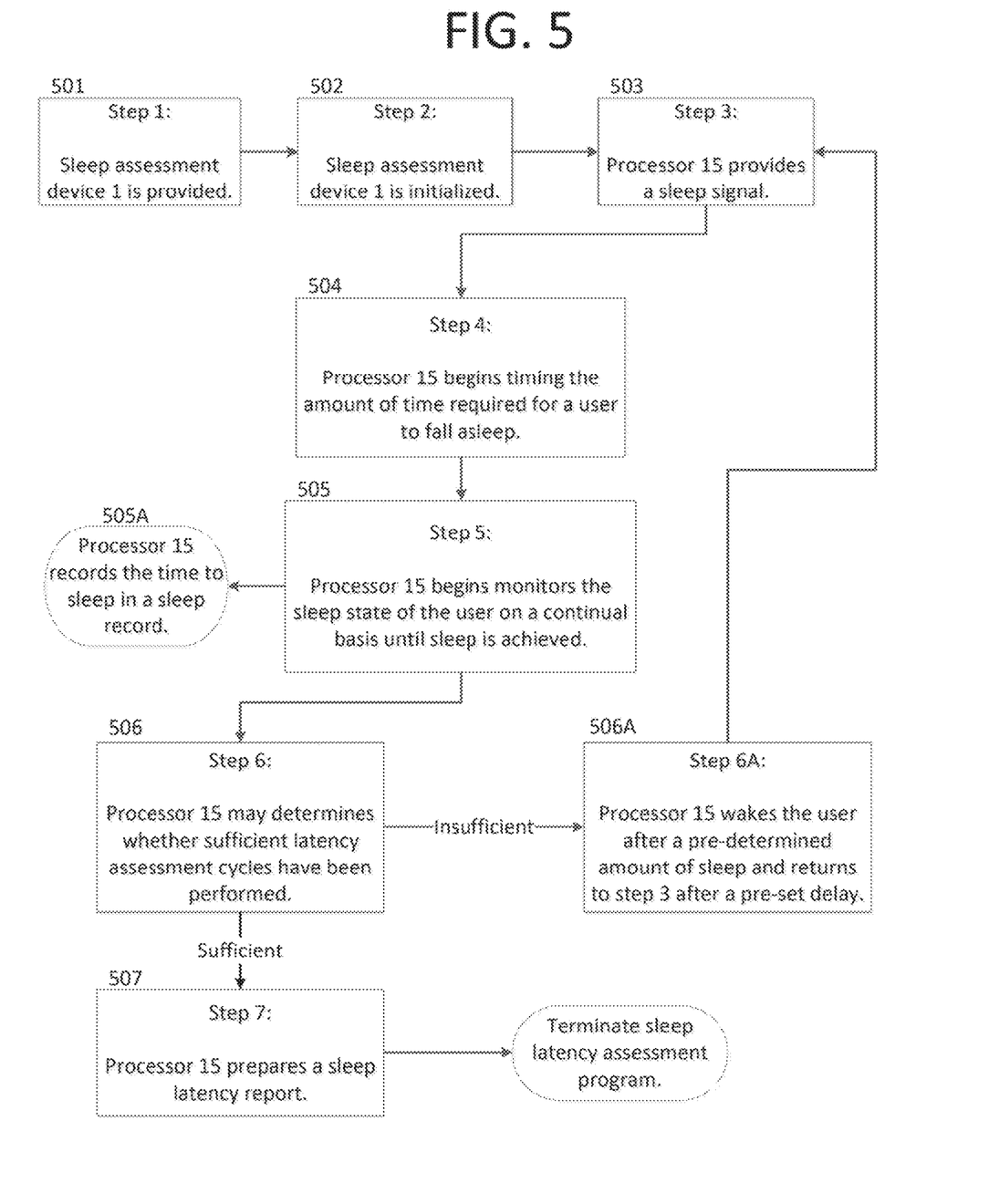
FIG. 5 is a flowchart showing a potential sequence of steps for a sleep latency assessment program in one example of the present disclosure.

FIG. 5 shows an example of a method for performing a sleep latency assessment. In some implementations of the present disclosure, a user's sleep latency may be tested by prompting the user to fall asleep periodically to determine how quickly a user achieves sleep. If a user successfully falls asleep within a predetermined period of time (e.g. 5 minutes) of being prompted, the system wakes the user, and sets another prompt for the following hour. The number of times the user successfully falls asleep can be useful for assessing their overall sleep latency and identifying potential sleep disorders.

At step 1, a sleep assessment device is provided, including at least one biometric sensor for detecting at least a heart rate of a user, respiration of a user, or movement of a user; and a processor 15 coupled to memory 11 (box 501 in FIG. 5). Each biometric sensor may be a contactless biometric sensor or a direct biometric sensor or a mixture of contactless and direct biometric sensors. At step 2, the sleep assessment device, including the at least one biometric sensor, is initialized (box 502).

At step 3, processor 15 provides a sleep signal for indicating to a user that they should now attempt to fall asleep (box 503). In some examples, the sleep signal may be an auditory prompt played by the sleep assistance device, such as one or more tones or a recorded audio instruction to begin trying to fall asleep. In other examples, a sleep signal may take the form of a written announcement appearing on display screen 5 or on another display screen of an external computing device in communication with sleep assessment device 1.

At step 4, processor 15 may begin timing how long it takes for a user to fall asleep (box 504). In some examples, processor 15 may note the time that the sleep signal was provided in a sleep record stored in memory 11. In other examples, processor 15 may start a timer in order to determine how long the user stays awake after receiving the sleep signal. However, any suitable method for tracking the time until a user falls asleep known to one of ordinary skill in the art may be used.

At step 5, processor 15 begins monitoring the sleep state of the user on a continual basis until sleep is achieved (box 505). For example, processor 15 may read one or more biometric sensors 19 that provide a direct indication that a user has lost consciousness. In other examples, biometric sensor(s) 19 may continually monitor and report other biometric information such as a user's heartrate, respiration rate or bodily movement from which a loss of consciousness may be deduced in a manner known to one of ordinary skill in the art. Once a user has been detected falling asleep, processor 15 may record the time that the user has fallen asleep or the elapsed time since the sleep signal was provided in a sleep record stored in memory 11 (box 505A).

At step 6, processor 15 may determine whether sufficient latency assessment cycles have been performed based on pre-set criteria (box 506). For example, processor 15 may continue the sleep latency assessment until a user has achieved sleep a prescribed number of times. Alternatively, processor 15 may continue the sleep latency assessment for a certain amount of time or until a desired time of day. If processor 15 determines that the sleep latency assessment should continue then the processor 15 may trigger an alarm tone at step 6A (box 506A). At step 6A, processor 15 may wake the user after a pre-determined amount of sleep (e.g. 5 minutes) in order to test the user's ability to fall asleep again. Any suitable mechanism for waking the user may be utilized. In some examples, processor 15 may play an alarm tone with an increasing volume until readings from biometric sensor(s) 19 indicate that the user has awoken. After providing an alarm tone and confirming that the user has awoken, processor 15 may return to step 3 in order to provide another sleep signal when the user should once again attempt to sleep. If processor 15 determines that the sleep latency assessment has concluded, then processor 15 may forgo the alarm tone and conclude the sleep latency assessment routine.

At step 7, if processor 15 determines that sufficient latency assessment cycles have been conducted, processor 15 may then prepare a report regarding the user's sleep latency, while allowing a user to continue sleeping (box 507). A sleep latency report may include summary statistics regarding a user's overall ability to fall asleep or may provide all of the data stored in the sleep record through the course of the sleep latency assessment. The sleep latency report may be transmitted through communications hardware 17 to a third party, such as a healthcare professional. This latency assessment data may be received by another device, where it can be stored in memory or another storage device, or can be displayed to a user. In other examples, a user's sleep latency assessment report may be maintained on sleep assessment device 1, but permission for third parties (e.g. a doctor or healthcare professional) to access the information via a network may be granted by a user. Such information may be useful for a healthcare professional to diagnose a potential sleep disorder or continue to monitor a user's progress during treatment for an already-diagnosed sleep disorder.

One of skill in the art will appreciate that the systems, methods and apparatuses outlined above may include various hardware and operating software, familiar to those of skill in the art, for running software programs as well as communicating with and operating any devices, including, for example, a biometric sensor, environmental sensors, a user interface, a computer network, a sound system, and any other internal or external devices. Such computerized systems may also include memory and storage media, and other internal and external components which may be used for carrying out the operations of this disclosure. Moreover, such computer systems may include one or more processors for processing and controlling the operation of the computer system, thus, embodying the processes of this disclosure. To that end, the processor, associated hardware and communications systems may carry out the various examples presented herein.

While the disclosed subject matter is described herein in terms of certain exemplary implementations, those skilled in the art will recognize that various modifications and improvements can be made to the disclosed subject matter without departing from the scope thereof. As such, the particular features claimed below and disclosed above can be combined with each other in other manners within the scope of the disclosed subject matter such that the disclosed subject matter should be recognized as also specifically directed to other implementations having any other possible permutations and combinations. It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

What is claimed:

1. A sleep assessment device comprising:
    at least one contactless biometric sensor for detecting at least one of a heart rate, respiration, or movement of a first user, the at least one contactless biometric sensor including one of an RF sensor, a laser, or an image-based monitoring system;
    a microphone configured to use beamforming to detect sound emanating from the first user;
    at least one speaker;
    a processor; and
    memory;
    wherein said processor is configured to detect the first user's sleep state by reading signals from said at least one contactless biometric sensor;
    wherein said processor is further configured to log information in a sleep record, including biometric information detected during a period the first user is sleeping;
    wherein said processor is configured to compare said logged information in said sleep record to a thumbprint of sleep patterns and output an indication of potential sleep disorders based on said comparison; and
    wherein said processor is further configured to generate a noise-masking sound based on sounds emanating from the first user that are detected by said microphone, and said at least one speaker is configured to play said noise-masking sound, and
    wherein said at least one speaker is one of a pair of headphones for a second user to wear or a pair of earbuds for the second user to wear.

2. The sleep assessment device of claim 1, wherein the thumbprint is a thumbprint of a normal sleep pattern.

3. The sleep assessment device of claim 1, wherein the thumbprint is a thumbprint of a known sleep disorder.

4. The sleep assessment device of claim 3, wherein the sleep disorder is one of: sleep apnea, sleep talking, sleep walking, and snoring.

5. The sleep assessment device of claim 1, wherein the processor is further configured to output a notification of a potential sleep disorder.

6. The sleep assessment device of claim 5, further comprising a transmitter for transmitting the notification of a potential sleep disorder.

7. The sleep assessment device of claim 1, further comprising at least one direct biometric sensor, wherein said processor is configured to detect the first user's sleep state by reading signals from said at least one direct biometric sensor.

8. The sleep assessment device of claim 7, wherein said at least one direct biometric sensor is a blood oxygen sensor.

9. The sleep assessment device of claim 2, wherein said processor is further configured to detect sound while the first user is sleeping and log sound information into said sleep record.

10. A method for providing an indication of a potential sleep disorder comprising:
    providing at least one contactless biometric sensor for detecting at least one of a heart rate, respiration, or movement of a first user, the at least one contactless biometric sensor being one of an RF sensor for directing RF signals towards the first user, measuring a strength of a backscattered signal, and analyzing the backscattered signal to determine a state of various vital signs of the first user over time, a laser for measuring minor skin deflections caused by the first user's heart rate and blood pressure, or an image-based monitoring system whereby skin deflections caused by heartbeats and blood pressure may be observed and analyzed over time through a camera;
    providing at least one microphone and using beamforming to detect sound emanating from the first user;
    providing at least one speaker;
    detecting the first user's sleep state by reading signals from said at least one contactless biometric sensor;
    logging information in a sleep record, including biometric information relating to the quality of the first user's sleep;
    comparing said logged information in said sleep record to a thumbprint of sleep patterns;
    determining whether a potential sleep disorder exists based on said comparison;
    providing an indication that a potential sleep disorder exists;
    generating a noise-masking sound based on noises that are detected by said at least one microphone; and
    playing said noise-masking sound through said at least one speaker;
    wherein said noise-masking sound is determined based on detected sounds emanating from the first user,
    wherein said at least one speaker is one of a pair of headphones for a second user to wear or a pair of earbuds for the second user to wear.

11. The method claim 10, further comprising providing at least one direct biometric sensor and reading signals from said at least one direct biometric sensor.

12. The method of claim 11, wherein said at least one direct biometric sensor is a blood oxygen sensor.

13. The method claim 10, further comprising:
    reading signals from said at least one microphone; and
    logging sound information in said sleep record.

14. The sleep assessment device of claim 1, wherein said speakers are further configured to play noise-canceling sounds.

15. The sleep assessment device of claim 14, wherein said noise-canceling sounds are modified according to said noise-masking sound.

\* \* \* \* \*